United States Patent [19]

Delaney et al.

[11] 3,937,803
[45] Feb. 10, 1976

[54] FLAVORED DENTAL CREAMS

[75] Inventors: Thomas James Delaney, Piscataway; William Grant Pierson, Flanders, both of N.J.

[73] Assignee: Colgate-Palmolive Company, New York, N.Y.

[22] Filed: Apr. 30, 1974

[21] Appl. No.: 465,461

Related U.S. Application Data

[63] Continuation-in-part of Ser. No. 295,068, Oct. 4, 1972, abandoned.

[52] U.S. Cl. .................................................. 424/49
[51] Int. Cl.² ........................................... A61K 7/16
[58] Field of Search ................................ 424/49–58

[56] References Cited
UNITED STATES PATENTS

| | | | |
|---|---|---|---|
| 1,082,681 | 12/1913 | Danner | 424/49 |
| 1,112,180 | 9/1914 | Westenfelter | 424/49 |
| 1,716,035 | 6/1929 | Donchi | 424/49 |
| 2,024,146 | 12/1935 | Crowther | 424/49 |
| 2,128,917 | 9/1938 | Crocker | 424/49 |
| 3,590,120 | 6/1971 | Muhler | 424/49 |

FOREIGN PATENTS OR APPLICATIONS

| | | | |
|---|---|---|---|
| 1,124,756 | 7/1956 | France | 424/49 |

*Primary Examiner*—Shep K. Rose
*Attorney, Agent, or Firm*—Steven J. Baron; Murray M. Grill; Herbert S. Sylvester

[57] ABSTRACT

Toothpaste containing sodium bicarbonate as the principal abrasive together with essential oil flavoring agent in a thickened water-glycerol vehicle in which the water:glycerol ratio is in the range of about 0.4:1 to 0.7:1.

11 Claims, No Drawings

FLAVORED DENTAL CREAMS

This application is a continuation-in-part of application Ser. No. 295,068, filed on Oct. 4, 1972 now abandoned.

Cross reference is made to copending applications Ser. Nos. 389,827, filed on Aug. 20, 1973; 295,073, filed on Oct. 4, 1972; and 419,741 filed on Nov. 28, 1973, whose entire disclosures are incorporated herein by reference.

This invention relates to toothpastes (i.e., dental creams) and more particularly to toothpastes containing dispersed particles of baking soda.

Baking soda has been employed in many fields and is a common household ingredient. In past years, its use in dentifrices particularly tooth powders, has been proposed but has not received much acceptance generally. The typical dentifrices which have significant consumer acceptance in recent years are toothpastes having a high content of water-insoluble abrasives such as dicalcium phosphate or other insoluble phosphates in an aqueous humectant base.

The development of a practical and effective baking soda toothpaste capable of consumer acceptability presents many special considerations. Among the factors which are to be considered are the unique character of baking soda chemically, physically and cosmetically when considered and employed as a toothpaste ingredient. For example, it is comparatively water-soluble and tends to release carbon dioxide in an aqueous system. It is extremely salty to the taste which is probably one of the more important factors in the purchase and use of a particular product. Other factors in formulation of a suitable product include the over-all cleaning and polishing power of the product, its stability and appearance combined with special care in manufacture, etc.

In accordance with various aspects of this invention, it is now possible to prepare a unique baking soda toothpaste which is effective in promoting hygiene in the oral cavity and capable of consumer desirability or acceptability by the public. Such product will have acceptable cleaning, polishing and other desirable characteristics so as to have a beneficial effect upon parts of the dentition (which may include the teeth and its surrounding or adjacent elements or structures including plaque, calculus, gingiva, mucous membranes, saliva, etc.). In particular, it tends to leave with the consumer a desirable clean mouth or clean mouth-feel effect. The product can be formulated so it is stable upon aging or storage without significant release of carbon dioxide, bubbles or other forms of undesirable separation or reaction. It is possible to produce and maintain a unique granular textured appearance comprising a substantially dispersed non-crystalline-appearing granulate which is due in part to the substantially homogeneous distribution of a sufficiently high concentration of macroscopic crystalline bicarbonate particles or granules in an otherwise smooth, continuous base or matrix, contributing to appearance, taste, effect and usage by the consumer.

One aspect of this invention relates to toothpastes (i.e. dental creams) containing about 20 to 60% of abrasive particles, principally sodium bicarbonate in a thickened water-glycerol vehicle, the water:glycerol ratio being in the range of about 0.4:1 to 0.7:1, said composition containing an essential oil flavoring agent which is present in an amount in the range of about 0.5 to 1.5%, preferably in the range of about 0.8 to 1.2%, e.g. 0.9 or 1%.

The toothpastes of this invention preferably contain at least about 25 to about 60%, more preferably at least about 35 to about 41% sodium bicarbonate as shown in the examples. The sodium bicarbonate is preferably the principal abrasive, by weight. The particle size of the sodium bicarbonate particles may vary; it is preferred that they be largely below about 0.4 mm in diameter, with a major proportion by weight being above about 0.01 mm in diameter. The vehicle in which the sodium bicarbonate particles are dispersed is preferably aqueous, but its amount and character are preferably such that the sodium bicarbonate is primarily in the undissolved solid state in the toothpaste. It will be understood, however, that when the teeth are brushed the sodium bicarbonate particles will tend to dissolve in the saliva.

Although the sodium bicarbonate particles are relatively soft as compared to most conventional abrasive particles used in toothpastes they do exert a mechanical cleaning effect on the teeth. For instance, in a radioactive dentin abrasion [RDA] test a toothpaste containing about 50% of bicarbonate of soda, as the sole abrasive, may show an RDA value of about 100 whereas when the abrasive-free vehicle of that toothpaste is tested similarly the RDA value is only in the neighborhood of 50.

Known dental creams containing relatively high proportions of sodium bicarbonate tend to have too salty a taste. This may possibly be due to the dissolution of part of the sodium bicarbonate in the water-glycerol vehicle in which water:glycerol ratio is about 2:1. When, however, this ratio is lowered to about 0.8:1 with a view to reducing the amount of dissolved sodium bicarbonate, the toothpaste becomes unstable on an aging at elevated temperatures (e.g. 110°F and 120°F). Thus, in aging tests of such toothpastes the oily flavor components (e.g. peppermint oil) incorporated in the dental cream show an increased tendency to separate from the rest of the cream; such separation has an adverse affect on appearance and flavor. Surprisingly, it is found that when the ratio is decreased still further, this separating tendency is markedly reduced while, at the same time, the toothpaste has a desirable less salty taste.

For some reason, unknown to applicants, the above-noted tendency to flavor separation is particularly marked when the sodium bicarbonate particles in the dental cream are of relatively large size, e.g. having particle diameters principally above 150 or 200 microns, and this invention is especially important in that case.

Other abrasives may also be present in addition to the sodium bicarbonate. Examples are finely divided silica, which may be of the crystalline or amorphous variety (e.g. micronized crystalline silica or silica gel, such as the silica gels sold as Syloid 63, Syloid 74, Syloid 244); alumina, such as hydrated alumina or alpha-alumina, zirconium silicate and amorphous or crystalline aluminosilicates. A particularly suitable compatible abrasive additive is calcium carbonate. The amount of added abrasive is generally less than the amount of sodium bicarbonate, e.g. in the range of about 5 to 25% of the toothpaste.

The toothpaste may also contain a small amount of titanium dioxide powder, which has been found to have a marked polishing effect on the teeth when used in the sodium bicarbonate toothpaste. The weight of titanium dioxide particles in the toothpaste is generally only a small fraction, e.g. less than about 10% and more than 0.1% on the weight of sodium bicarbonate, preferably about 0.1 to 5.0%, optimally about .5 to 2% thereof but is generally above about 0.1% of the weight of the toothpaste. For instance, the amount of $TiO_2$ may be included in amounts up to about 6.0%, preferably about 0.2 to 0.6% of the weight of the toothpaste. The particle size of the $TiO_2$ is preferably below 1 micron, e.g. 0.05–0.8 micron.

Examples of suitable flavoring oils are oils of spearmint, peppermint, wintergreen, sassafras, clove, sage, eucalyptus marjoram, cinnamon, lemon and orange, as well as sodium methylsalicylate. Preferably the amount of flavoring oil is above about 0.5% and below about 2%, e.g. about 0.8 to 1.2%.

The water-glycerol vehicle preferably contains a thickening agent (e.g. a gelling agent). The amount thereof can be adjusted depending upon the amount of bicarbonate present and $TiO_2$ where included, in accordance with procedures known in the art with respect to thickening of the vehicle.

The calculation with respect to the amount of sodium bicarbonate and $TiO_2$ may be readily gleaned from the examples and from the respective ratios of the other ingredients, viz., the water-glycerol ratio (i.e., 0.4:1 to 0.7:1), flavoring oil (i.e., 0.5 to 2.0%), thickening agent (i.e., 0.5 to 2.0%), surface-active agent (i.e., .05 to 5%) and the like.

Gelling agents for toothpaste vehicles are well known in the art. These are often high polymers (e.g. gums or other thickening agents) which are soluble or swellable in water or aqueous medium. Sodium carboxymethylcellulose has given excellent results. Other materials are gum tragacanth, gum arabic, gum karaya, sodium alginate, hydroxyethyl cellulose, methyl cellulose, ethyl cellulose, carrageen and other polysaccharides, polyvinyl pyrollidones or such thickening agents as "Veegum" (a complex magnesium aluminum silicate). The amount of thickening agent used in the practice of this invention is preferably sufficient to impart to the mixture the pasty consistency, body and the non-tacky nature which is characteristic of conventional dental creams or toothpastes. As is well known, such dental creams are extrudable from ordinary collapsible toothpaste tubes to form a ribbon of substantial thickness (e.g. about 3/8 inch) which if left undisturbed, substantially retains its original thickness over a period of, say, one minute or more (and does not penetrate substantially into the bristles of a toothbrush when resting on the ends of such bristles for a similar period); but which preferably offers no substantial resistance to brushing or to deformation when, for instance, one touches it lightly with a finger; and which has little tack, in that it does not tend to form a string when the finger is pulled away from the ribbon. The proportion of thickening agent is often within the range of about 0.5 to 2%, such as about 0.8 to 1.5%, of the toothpaste.

An organic surface active agent is preferably used in the compositions of the present invention to aid in the prophylactic action and in the thorough dispersion of the composition throughout the oral cavity, and to improve cosmetic acceptability and detersive and foaming properties. Among these are water-soluble salts of the higher alkyl sulfates, such as sodium lauryl sulfate or other suitable alkyl sulfate having 8 to 18 carbon atoms in the alkyl group; water-soluble salts of sulfonated monoglycerides of higher fatty acids such as sodium coconut monoglyceride sulfonate or other suitable sulfonated monoglyceride of a fatty acid of 10 to 18 carbon atoms; salts of amides of higher fatty acid (e.g. 12 to 16 carbon atom acids) with lower aliphatic amino acids (e.g. taurine or sarcosine) or other amino acid of 2 to 6 carbon atoms, such as sodium-N-methyl-N-palmitoyl tauride, sodium N-lauroyl, N-myristoyl or N-palmitoyl sarcosinates; water-soluble salt of the esters of such fatty acids with isethionic acid or with glycerol monosulfate, such as the sodium salt of the monosulfated monoglyceride of hydrogenated coconut oil fatty acids; water-soluble salts of olefin sulfonates, e.g. alkene sulfonates or hydroxyalkane sulfonates or mixtures thereof having 12 to 18 carbon atoms in the carbon chain of the molecule; water-soluble soaps of higher fatty acids such as those of 12–18 carbon atoms e.g. coconut fatty acids. The cation of the salt may be, for instance, sodium (which is preferred) potassium or mono-di- or triethanolamine. Mixtures of surface-active agents may be used. A particularly suitable mixture which provides a high foaming powder with little or no irritating effect comprises a higher alkyl sulfate and a higher fatty acid sarcosinate, e.g. in a ratio of about 1:2 to 2:1, such as about 1:1; instead of all or part of the sarcosinate a higher fatty acid monoglyceride sulfonate may be present.

Other suitable surface-active materials include nonionic agents such as condensates of sorbitan monostearate with approximately 60 moles of ethylene oxide, condensates of ethylene oxide with propylene oxide condensates of propylene glycol (available under the trademark "Pluronics") and amphoteric agents such as quaternized imidazole derivatives which are available under the trademark "Miranol" such as Miranol $C_2M$. Cationic surface-active germicides and anti-bacterial compounds may also be used. Such compounds include di-isobutyl-phenoxyethoxyethyl dimethyl benzyl ammonium chloride, benzyl dimethyl stearyl ammonium chloride, tertiary amines, having one fatty alkyl group (of from 12 to 18 carbon atoms) and two (poly) oxyethylene groups attached to the nitrogen (typically containing a total of from about 2 to 50 ethenoxy groups per molecule) and salts thereof with acids, and compounds of the structure:

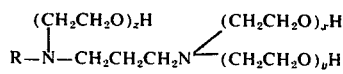

where R is a fatty alkyl group consisting from about 12 to 18 carbon atoms, and x, y and z total 3 or higher, as well as salts thereof with mineral or organic acids. It is preferred to use from about 0.05 to 5 percent by weight of the foregoing surface-active materials in the instant dentifrice preparations.

The proportion of surface-active agent is preferably within the range of about 0.05–5% of the toothpaste, more preferably in the range of about 1 to 3%, such as about 1-½ to 2%.

In accordance with certain aspects of this invention, cationic antibacterial agents are included in the compositions of the present invention. Such agents include:

$N^1$-(4-chlorobenzyl)-$N^5$-(2,4-dichlorobenzyl) biguanide p-chlorophenyl biguanide
4-chlorobenzyhydryl biguanide;
4-chlorobenzhydrylguanylurea;
N-3-lauroxypropyl-N⁵-p-chlorobenzylbiguanide;
1-(lauryldimethylammonium)-8-(p-chlorobenzyl-dimethylammonium) octane dichloride;
5,6-dichloro-2-guanidinobenzimidazole;
N¹-p-chlorophenyl-N⁵-laurylbiguanide;
5-amino-1,3-bis (2-ethylhexyl)-5-methylhexahydropyrimidine; cetyl pyridinium chloride and their non-toxic acid addition salts, particularly the fluorides and the dihydrogen fluorides. 1,6-di-(p-chlorophenylbiguanidohexane) is particularly preferred. These agents may be used in amounts ranging from about 0.01 to 5 percent by weight or the dentifrice.

A sweetening agent may be present. Suitable sweetening agents include lactose, maltose, sorbitol, sodium cyclamate, perillartine, saccharine and ammoniated glycyrrhizin (e.g. its monoammonium salt). At present it is preferred to use a noncariogenic type of sweetening agent such as saccharine, e.g. in amounts of 0.1 to 0.2%.

The dental cream may also contain a fluoride-containing anticaries agent. There are many water-soluble inorganic salts which are suitable sources of fluoride ions. Among these are sodium, potassium, ammonium, and lithium and amine fluorides. The monofluorophosphate salts are also useful and include $Na_4P_3O_9F$, $K_4P_3O_9F$, $(NH_4)_4P_3O_9F$, $Na_3KP_3O_9F$, $(NH_4)NaP_3O_9F$, and $Li_4P_3O_9F$. Complex water-soluble fluoride-containing salts such as fluorosilicate (i.e., $Na_2SiF_6$), fluorozirconate (i.e., $Na_2ZrF_6$), fluorostannite (i.e., $KSnF_3$), fluoroborate (i.e., $NaBF_4$), fluorotitanate (i.e., $NaTiF_5$), and fluorogermanate (i.e., $K_2GeF_6$) may also be useful. The fluoride ion may also be supplied by an organic fluoride which yields fluoride ions in water. Suitable organic compounds include mono-, di-, and triethanolamine hydrofluoride. These materials are present in an effective but non-toxic amount, usually within the range to provide about 0.01 to 1 percent by weight of the water-soluble fluorine content thereof to the dentifrice. Sodium fluoride, and sodium monofluorophosphate are the preferred compounds.

Various other materials may be incorporated into the dentifrice preparations of this invention. Examples thereof are coloring and whitening agents, preservatives, silicones, chlorophyll compounds, and mixtures thereof, and other constitutents. These adjuvants are incorporated in the instant compositions in amounts which do not substantially adversely affect the properties and characteristics desired and are selected and used in proper amount depending upon the particular type of preparation involved.

The following Examples are given to illustrate this invention further. In this application all proportions are by weight unless otherwise indicated.

EXAMPLE 1

A toothpaste is prepared by forming a gel by mixing a gelling agent, in this case sodium carboxymethylcellulose ("CMC"), with glycerol and water (in the presence of a sweetener, sodium saccharin, and a preservative, sodium benzoate), adding sodium bicarbonate (baking soda) chalk, and titanium dioxide powder to the gel, then adding a surfactant and peppermint flavor (rich in peppermint oil) and thereafter degassing the mixture under vacuum. The proportions used are: 40% baking soda, 5% chalk, 0.4% titanium dioxide, 15.4% water, 33.5% glycerol, 1% sodium lauryl sulfate, 2% of a solution of 35% sodium N-lauroyl sarcosinate in a mixture of 35% water and 30% glycerol, 1.1% CMC, 0.9% water insoluble flavor, 0.5% sodium benzoate and 0.2% sodium saccharin.

The baking soda powder in U.S.P. grade having the following particle size distribution in which percentages represent the cumulative per cent retained on the named sieve, and sieve sizes are U.S. Standard): No. 45 Sieve, trace; No. 70 sieve (sieve opening 210 microns), 27%; No. 80 sieve (sieve opening 177 microns) 66.5%, No. 100 sieve (sieve opening 149 microns), 92.5%; No. 170 sieve (sieve opening 88 microns), 99%.

The chalk is a grit-free U.S.P. Non Fer Al Chalk containing at least 98% $CaCO_3$ with no more than 0.2% insoluble in dilute HCl. Its particle size is such that over 99% passes through a U.S. Standard No. 325 mesh sieve, the particles being principally in the 1 to 10 micron size, the average particle size being about 3 microns.

The titanium dioxide used is a grit-free anatase powder at least 99.0% of which passes through a No. 325 U.S. Standard sieve and whose mean particle diameter (as measured on a Kahn sedimentation balance) is below 1 micron. Microscopic measurements indicate its average particle diameter is 0.3 micron.

EXAMPLE 2

Example 1 is repeated except that the proportion of baking soda is increased to 41%, the proportion of glycerol is correspondingly reduced to 32.5%, and a smaller particle size baking soda is used.

The baking soda powder is U.S.P. grade having the following particle size distribution (in which percentages represent the cumulative per cent retained on the named sieve, and sieve sizes are U.S. Standard) No. 45 sieve (sieve opening 350 microns), trace; No. 100 sieve (sieve opening 149 microns), 0.5%; No. 170 sieve (sieve opening 88 microns), 20%, No. 200 sieve (sieve opening 74 microns), 35%; No. 325 sieve (sieve opening 44 microns), 70%; No. 400 sieve, 80%.

EXAMPLE 3

Example 1 is repeated except that the proportion of chalk is increased to 10% and the proportion of baking soda is correspondingly lowered to 35%.

EXAMPLE 4

Example 1 is repeated except that the proportion of glycerol is increased to 37.5%, the proportion of water is reduced to 10.4% and the amount of baking soda is 41%.

EXAMPLE 5

Example 1 is repeated except that the proportion of glycerol is increased to 43.4%, the proportion of water is reduced to 10.4% and the amount of baking soda is 35%.

EXAMPLE 6

This Example illustrates the use of unlined aluminum toothpaste tubes with certain baking soda toothpastes.

a. A toothpaste is made up (using, for instance, the method of Example 1) of 40% of the baking soda powder (of Example 1) 5% of calcium carbonate, (of Example 1), 0.4% titanium dioxide of Example 1, 33.4% glycerol, 15.4% deionized water, 1.1% CMC (Hercules 7MF), 2% of a solution of 35% sodium N-lauroyl sarcosinate in a mixture of 35% water and 30% glycerol, about 1% sodium lauryl sulfate, 1% flavor (water-insoluble essential oil flavoring agent; e.g., essential oil mixture rich in peppermint oil), 0.5% sodium benzoate, and 0.2% sodium saccharin.

b. Example 6a is repeated except that 0.5% of fumed silica (Cab-O-Sil) is included, the amount of calcium carbonate is raised to 10%, the amount of baking soda is decreased to 35% and amount of glycerol is decreased to 32.9%.

c. Example 6b is repeated except that the amount of calcium carbonate is decreased to 5% and the amount of glycerol is raised to 37.9%.

d. Example 6a is repeated four times, with additional inclusion of various proportions of non-acidic dicalcium phosphate dihydrate in the formulation, i.e., in amounts of 0.04%, 0.2%, 0.4% and 0.8% (based on the weight of the formulation without said phosphate); the first case (0.04%) the titanium dioxide is omitted. The dicalcium phosphate dihydrate is of dentifrice grade and has an average particle diameter of about 4 microns and its pH (measured in 20% slurry thereof in water) is in the range of 7.2 to 7.9; it yields phosphate ions on contact with water.

e. Example 6a is repeated with the additional inclusion of insoluble sodium metaphosphate in the formulation in the amount of 0.8% (based on the weight of the formulation without said phosphate). The insoluble sodium metaphosphate is of dentifrice grade having an average particle size of about 5 microns; its pH (measured in 20% slurry thereof in water) is in the range of 5.3 to 6.3; it yields phosphate ions on contact with water.

f. Example 6a is repeated except that 5% micronized silica is substituted for the calcium carbonate, a different essential oil flavor is used, the amount of flavor is 0.9% and the amount of glycerol is 33.5%.

g. Example 6a is repeated except that 3% micronized silica is included, the calcium carbonate is omitted, the amount of baking soda is increased to 42%, and the toothpaste contains 0.9% of an essential oil flavor.

h. Example 6a is repeated except that 5% precipitated silica is substituted for the calcium carbonate:

i. Example 6a is repeated except that 5% anhydrous dicalcium phosphate is substituted for the calcium carbonate, the toothpaste contains 0.9% of an essential oil flavor and the amount of glycerol is increased to 33.5%). The anhydrous dicalcium phosphate is a fine non-acidic powder of dentifrice grade. Its pH (as measured on a 20% slurry thereof in water) is 7.6–7.8; it yields phosphate ions, in low concentration, on contact with water.

j. Example 6a is repeated except that 5% zirconium silicate is substituted for the calcium carbonate (with minor change in proportion and type of flavor).

k. Example 6a is repeated except that 5% beta phase calcium pyrophosphate is substituted for the calcium carbonate. The calcium pyrophosphate is a fine powder of dentifrice grade. Its pH (as measured on a 20% slurry thereof in water) is 5.2–5.3.

Each of the foregoing toothpastes is placed in an individual toothpaste tube of unlined aluminum of high purity (99.7% Al or purer) and aged. On aging at 120°F the tube filled with the 6a toothpaste tends to swell or is found to have a foamy product film in contact with the inner aluminum walls of the tube, tubes filed with the 6b, c, d, f, g, h, i, j, and k toothpastes do not show such effects. The 6e toothpaste shows substantially less tendency to react with the walls of the tube than the 6a toothpaste.

The fumed silica (as in Example 6b) is described in Encyclopedia of Chemical Technology Kirk-Othmer 2nd Edition, Vol. 18 at pages 62 and 67, for instance. It is within the broader scope of the invention to use the fumed silica in baking soda toothpaste from which the compatible water-insoluble abrasive (such as calcium carbonate) has been omitted, in unlined aluminum tubes. It is also within the broader scope of the invention to employ, in place of the fumed silica, very finely dispersed or dissolved silica in other forms such as alkali metal silica such as sodium silicate, e.g. hydrated sodium silicate supplied in flake form containing $Na_2O \cdot SiO_2 \cdot H_2O$ in a ratio of about 1:2–3.2:5, or sodium silicate solutions (water glass) such as those in which the $Na_2O:SiO_2$ ratio is at least about 1:2, or sodium silicate formed in situ in the dental cream, or colloidal silica or precipitated silica (see Encyclopedia of Chemical Technology, Kirk-Othmer, 2nd edition Vol. 18, pages 63 and 66–67, for instance) or other silicate.

The dicalcium phosphate dihydrate of Example 6d is a commercial stabilized dentifrice grade of this material. A description of the method of preparation of dicalcium phosphate dihydrate and of its stabilization is found in U.S. Pat. of Schlaeger et al No. 3,169,096 Feb. 9, 1965, whose disclosure is incorporated herein by reference. See also "Cosmetic Science" Vol. 1 pub. 1972 (Wiley Interscience) edited by Balsam and Sagarin pages 477–479. One typical analysis of dicalcium phosphate dihydrate indicates that its content of water-soluble material is 0.18% (and its percent water-solubles expressed as $P_2O_5$ is 0.11%). A typical stabilizer content is a mixture of about 1-2% of sodium calcium pyrophosphate and a smaller amount, e.g. about 0.4%, of pyrophosphoric acid.

The insoluble sodium metaphosphate of Example 6e is a commercial dentifrice grade of this material. Its method of preparation and properties are described in the previously cited "Cosmetic Science" at pages 480–481 and "Phosphorus and Its Compounds" by Van Wazer Vol. 2 pub. 1961 (Interscience) pages 1652–1653.

The anhydrous dicalcium phosphate of Example 10i and the calcium pyrophosphate of Example 6k are commercial dentifrice grades of these materials. See the previously cited "Phosphorus and Its Compounds" page 1651 and "Cosmetic Science" pages 479–480.

EXAMPLE 7

Example 6a is repeated except that the toothpaste contains added anhydrous disodium phosphate (incorporated as a water-soluble powder) in amount of (a) 0.05% and (b) 0.01%, the amount of water in the toothpaste being adjusted accordingly to total 100%. In each case, on aging in unlined aluminum tubes (as in Example 6) the filled tubes do not swell or gas and (after 9 weeks aging at 120°F.) the inner walls of the tubes are found to be gold-colored, the wall color in the tube containing the 7b toothpaste being very light. On inspection of the inner walls of the unlined aluminum tubes containing the 6d toothpastes (again after 9 weeks at 120°F.) they are found to be dark (when the pastes contain 0.8% or 0.4% of the dicalcium phosphate dihydrate) or golden (when the tubes contain 0.04% and 0.2% of the dicalcium phosphate dihydrate); on inspection of the inner walls of the unlined aluminum tubes containing the 6k toothpaste they are found to be golden after 3 and 6 weeks aging at 120°F. and dark after 9 weeks of such aging. It is belived that the toothpastes containing the dicalcium phosphate dihydrate contain (or form, on aging) small amounts of dissolved phosphate ions (e.g. orthophosphate and/or pyrophosphate) which may act on the aluminum walls, or on the aluminum oxide layer on said walls, to form a protective layer thereon. The amount of dissolved phosphate ion present in the preferred compositions is sufficient to inhibit the gas-forming reaction between the alkaline toothpaste composition and the aluminum walls of the tube but the amount of the phosphate or acidic ingredient therein is insufficient to cause a gas-forming reaction (e.g. resulting in swelling or bursting of the tube) between the ingredients of the toothpaste; the tendency for the latter reaction can, of course, be tested by placing the composition in a suitably lined aluminum tube (whose walls are thus substantially inert to the composition) and aging for several weeks (e.g. 9 weeks) at an elevated temperature (e.g. 120°F.).

Storage of the toothpastes of other types in unlined aluminum tubes is discussed in such patents as U.S. Pat. Nos. 3,662,060 and 3,678,155 and Austrian Pat. No. 267,070. As is well known to consumers of toothpastes, aluminum toothpaste tubes are squeezable and deformable to express the toothpaste from the nozzle of the tube and the main body of the tube is of relatively thin, ductile, aluminum.

The baking soda used in the Examples is a product made by precipitation from solution (as by treating a sodium carbonate solution with carbon dioxide to precipitate the bicarbonate) followed by drying, curing with carbon dioxide gas and screening to the desired particle size (generally without substantial crushing or pulverizing).

These particles are generally monoclinic crystals or tablets or conglomerates thereof (e.g. twinned crystals) some having projecting spike-like portions of generally rhombohedral shape with many reentraut angles.

The toothpastes of the foregoing Examples are non-effervescent. Thus when diluted with water they do not actively evolve bubbles of carbon dioxide.

The toothpastes of this invention have an alkaline pH, generally in the range of about 8.5 to 9.5, usually below about 9.1.

The dentin abrasion of the toothpastes may be determined by the procedure based on a radioactive technique described by Grabenstetter et al in the "Journal of Dental Research", Volume 37, P. 1060 (1958) as modified by the description by Stookey et al. in the "Journal of Dental Research," Volume 47, page 524 (July-August 1968).

In the preparation of the toothpastes of this invention the abrasive particles are blended with all or part of the vehicle and then subjected to subatmospheric pressure (e.g. a vacuum of about 26 to 30 inches of mercury, corresponding to an absolute pressure or up to about 100 mm Hg) remove dispersed gas. The vacuum treatment is, however, discontinued, despite continued formation of gas bubbles under vacuum, before the pH (i.e. the pH of the vacuum treated mixture minus the pH of the mixture without vacuum treatment) reaches one pH unit and preferably less, e.g. 1/2 unit; this avoids decomposition of sodium bicarbonate and production of sodium carbonate during degassing.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A toothpaste containing about 20 to 60% of abrasive particles comprising at least about 25% sodium bicarbonate in a vehicle containing sufficient liquids and including a water-glycerol mix, the water-glycerol ratio being in the range of about 0.4 to 0.7:1, said vehicle consisting essentially of about 5 to 35% water and said glycerol and a sufficient amount of gelling or thickening agent to impart to the dental cream the pasty consistency, body and non-tacky nature which is characteristic of conventional dental creams or toothpastes, said toothpaste containing a water-insoluble essential oil flavoring agent in the range of about 0.5 to 1.5%, said sodium bicarbonate being primarily in the undissolved solid state, said dental cream having a granular textured appearance comprising a substantially dispersed non-crystalline appearing granulate of macroscopic crystalline bicarbonate granules in an otherwise smooth continuous matrix.

2. Toothpaste as in claim 1 containing about 35 to 41% sodium bicarbonate.

3. Toothpaste as in claim 1 containing sodium bicarbonate of particle diameter principally above 150 microns but below 0.4 mm.

4. Toothpaste as in claim 3 containing sodium carboxymethylcellulose as gelling agent.

5. Toothpaste as in claim 1 containing a compatible surfactant.

6. Toothpaste as defined in claim 1 wherein said bicarbonate has a particle size largely below about 0.4 mm in diameter.

7. Toothpaste as defined in claim 1 wherein a major proportion by weight of said bicarbonate has a particle size above about 0.01 mm in diameter.

8. Toothpaste as defined in claim 1 additionally containing about 5 to 25% of a further abrasives ingredient.

9. Toothpaste as defined in claim 1 additionally containing less than about 25% calcium carbonate.

10. A toothpaste as defined in claim 1 wherein said vehicle contains a thickening agent.

11. Toothpaste as defined in claim 1 wherein sodium bicarbonate is generally monoclinic crystals, some of which have projecting spike-like portions of generally rhombohedral shape with many reentraut angles.

* * * * *